United States Patent [19]

Smith et al.

[11] Patent Number: 5,635,541
[45] Date of Patent: Jun. 3, 1997

[54] ELEVATED PRESSURE AIR SEPARATION UNIT FOR REMOTE GAS PROCESS

[75] Inventors: Arthur R. Smith, Telford; John L. Dillon, IV, Kutztown; Donald W. Woodward, New Tripoli, all of Pa.

[73] Assignee: Air Products and Chemicals, Inc., Allentown, Pa.

[21] Appl. No.: 489,398

[22] Filed: Jun. 12, 1995

[51] Int. Cl.$^6$ .................................................. C07C 27/06
[52] U.S. Cl. ........................... 518/703; 518/702; 518/700
[58] Field of Search ................................. 518/702, 703

[56] References Cited

U.S. PATENT DOCUMENTS

| | | | |
|---|---|---|---|
| 4,341,069 | 7/1982 | Bell et al. | 60/39.02 |
| 4,888,131 | 12/1989 | Goetsch et al. | 252/373 |
| 4,927,856 | 5/1990 | Elion | 518/702 |
| 5,081,845 | 1/1992 | Allam et al. | 62/24 |
| 5,160,456 | 11/1992 | Lahn et al. | 252/373 |
| 5,251,451 | 10/1993 | Xu et al. | 62/25 |
| 5,388,395 | 2/1995 | Scharpf et al. | 60/39.02 |

OTHER PUBLICATIONS

Ansell, L. L., Eisenberg, B. and Bauman, R. F. "Liquid Fuels from Natural Gas—An Update of the Exxon Process" presented at the Council on Alternate Fuels, Apr. 26–29, 1994.

Tijm, P. J. A., Marriott, J. M., Senden, M. M. G., van Wechem, H. M. H., "Shell Middle Distillate Synthesis The Process, The Products, The Plant" presented at the Council on Alternate Fuels, Apr. 26–19, 1994.

*Primary Examiner*—Gary Geist
*Assistant Examiner*—Srenni Padmananabhan
*Attorney, Agent, or Firm*—Willard Jones, II

[57] ABSTRACT

The present invention is an improvement to a process for the conversion of natural gas to produce higher molecular weight hydrocarbon products, wherein the natural gas is partially oxidized to produce a synthesis gas comprising carbon monoxide and hydrogen, wherein the synthesis gas is catalytically reacted to produce the higher molecular weight hydrocarbon products, wherein the conversion process generates excess steam and wherein oxygen used to partially oxidize the natural gas is produced by an air separation process. The improvement is characterized by operating such air separation process at an elevated pressure so that the feed air to the air separation process is compressed to between 8 and 20 Bar(a); expanding at least a portion of the excess steam generated by the conversion process to generate work and using at least a portion of the generated work to drive the compression requirements of the air separation process.

11 Claims, 2 Drawing Sheets

ELEVATED PRESSURE AIR SEPARATION UNIT FOR REMOTE GAS PROCESS

FIELD OF THE INVENTION

The present invention relates to a process for the conversion of remote gas into higher molecular weight hydrocarbon products, such as quality refinery feedstocks. In particular, the present invention relates to the integration of an air separation process into such remote gas process.

BACKGROUND OF THE INVENTION

The remote gas process is the process to chemically convert natural gas at locations remote from world markets to ultrahigh quality refinery feed stocks or finished products. These products can be shipped, stored and consumed in conventional facilities. Liquefied natural gas has been the method of choice for many years for recovering and shipping remote natural gas. Other alternatives are conversion to methanol, gasoline or ammonia. The high value products, compared to the alternatives, make the remote gas process a very viable process (even though the thermal efficiency is lower) and the subject of many recent studies. The first commercial plant is the Shell Middle Distillate Synthesis plant started in May 1993 in Bintulu, Sarawak, in eastern Malaysia. In this case, natural gas is converted to synthesis gas using non-catalytic partial oxidation and the synthesis gas is converted via Fischer-Tropsch to premium middle distillate products including wax and specialty chemicals. This is a 500,000 metric ton per year facility. Another remote gas process is Exxon's Advanced Gas Conversion process where syngas is produced from combined catalytic partial oxidation/reforming as feed stock to their heavy paraffin synthesis Fischer-Tropsch step followed by hydroisomerization to produce white oil.

The remote gas process normally requires a syngas step in which oxygen from an air separation unit is used to partially oxidize the natural gas, sometimes with steam methane reforming. The air separation unit is typically a conventional low pressure cycle with essentially no air separation unit nitrogen utilization. The Bintulu remote gas process unit has such an air separation unit.

It is the object of this invention to lower the capital investment of the air separation unit compared to common practice or to lower the capital investment of the total remote gas process facility through integration schemes with the air separation unit. It is asserted that an elevated pressure air separation unit may be defined as having feed air compressed between 8 and 30 Bar(a) [800 and 3,000 kPa (absolute)] and preferably between 12 and 18 Bar(a) [1,200 and 1,800 kPa(absolute)]. There is a prevailing industry-wide belief that elevated pressure air separation unit cycles only make sense in cases where the available high pressure nitrogen is utilized at high pressures, such as gas turbine integrations for power generation. Industry has not yet come to realize that, since power efficiency is not of utmost importance for remote gas process, elevated pressure air separation unit cycles are the low cost option, even if high pressure nitrogen is not utilized at high pressure.

A second objective is to more effectively utilize the excess energy (usually in the form of steam) available in the remote gas process.

U.S. Pat. No. 4,888,131 (Goetsch, et al.) and U.S. Pat. No. 5,160,456 (Lahn, et al.) both describe the remote gas process syngas generation process, but make no mention of the air separation unit or air separation unit integration. Further information on the Exxon remote gas process is also taught in a paper by Ansell, L. L., Eisenberg, B. and Bauman, R. F., entitled "Liquid Fuels from Natural Gas—An Update of the Exxon Process", presented at the Council On Alternate Fuels, Apr. 26–29, 1994.

A paper by Tijm, P. J. A., Marriott, J. M., Senden, M. M. G., van Wechem, H. M. H., entitled "Shell Middle Distillate Synthesis The Process, The Products, The Plant", presented at the Council On Alternate Fuels, Apr. 26–29, 1994, gives a summary of the Shell remote gas process, but does not mention any details on the air separation unit.

U.S. Pat. No. 5,251,451 (Agrawal, et al.) describes a typical elevated pressure air separation unit and the integration with gas turbines, but does mention remote gas process.

U.S. Pat. No. 5,081,845 (Allam, et al.) describes an elevated pressure air separation unit with high pressure nitrogen expanded for shaft power and/or refrigeration. Further, the patent teaches to heat high pressure nitrogen with available heat energy and to expand this stream for additional shaft power. It also teaches integration with integrated gasification combined cycle. Power efficiency may be improved by introducing the high pressure nitrogen to the gas turbine combustor. No mention is made of the remote gas process.

U.S. Pat. No. 5,388,395 (Scharpf, et al.) teaches the use of an elevated pressure air separation unit with high pressure nitrogen expanded for shaft power and refrigeration. It also teaches blending cool expanded nitrogen with the gas turbine inlet air to improve shaft power, and also to first saturate the high pressure nitrogen with water before expanding. It mentions integration with an integrated gasifier combined cycle by having the expanded nitrogen provide refrigeration for inlet gas turbine air, but there is no mention of remote gas process.

Waste nitrogen chilling towers have been commonly used in air separation units for years to provide chilled water for feed air cooling, but have not been used as proposed.

In summary, examples have been provided describing the remote gas process and examples have been provided describing the elevated pressure air separation unit and methods of utilizing air separation unit high pressure nitrogen for improved power efficiency, but nowhere is described the use of an elevated pressure air separation unit in conjunction with remote gas process. Conventional thinking for those skilled in the remote gas process art and the air separation unit art is that elevated pressure air separation unit cycles are only economical for gas turbine power generation cycles where high pressure nitrogen is introduced to the gas turbine combustor and that the air separation unit of choice is the low pressure air separation unit as demonstrated in the Bintulu project. The point being overlooked is that for a remote gas process, power is valued comparatively low and low capital expenditures are very important. Also overlooked is the fact that elevated pressure air separation units are lower in capital than low pressure air separation units, especially in large sizes, and that no recovery of energy from the high pressure nitrogen in an elevated pressure air separation unit is justifiable when recovering that energy cannot, in turn, be used to further reduce equipment costs.

SUMMARY OF THE INVENTION

The present invention is an improvement to a process for the conversion of natural gas to produce higher molecular weight hydrocarbon products, wherein the natural gas is partially oxidized to produce a synthesis gas comprising carbon monoxide and hydrogen, wherein the synthesis gas is catalytically reacted to produce the higher molecular weight hydrocarbon products, wherein the conversion process generates excess steam and wherein oxygen used to partially oxidize the natural gas is produced by an air separation process. The improvement is characterized by operating such air separation process at an elevated pressure so that the feed air to the air separation process is compressed to between 8 and 30 Bar(a) [800 and 3,000 kPa(absolute)]; expanding at least a portion of the excess steam generated by the conversion process to generate work and using at least a portion of the generated work to drive the compression requirements of the air separation process.

The present invention also relates to uses of the high pressure nitrogen produced by the elevated pressure air separation process. In one use, the high pressure nitrogen is reduced in pressure and fed to a water chilling tower. In another use, the high pressure nitrogen is expanded to generate work. Such work can be used to generate electricity or to drive compression requirements of the process. Finally, the high pressure nitrogen is heated by another portion of the excess steam prior to work expansion thereby producing additional work upon expansion.

DETAILED DESCRIPTION OF THE INVENTION

The present invention is a process to integrate the remote gas process with an elevated pressure air separation unit for the purpose of reducing the overall equipment costs. Integration schemes are included that involve recovering excess energy from the remote gas process and recovering energy from the air separation unit high pressure nitrogen. In the process of the present invention, at least a portion of the excess steam produced in the remote gas process, which is usually condensed to recover water while producing no work, is used to increase the air supply pressure to the air separation unit and, thus, allowing the use of an elevated pressure air separation process configuration. Since the capital cost of the condenser is significant, the capital costs of the integrated process can be decreased. The increased main air compressor and driver costs are more than offset by decreased air pretreatment, main heat exchanger, product compressor and driver costs. The subject invention consists of four embodiments; FIGS. 1A through 1D illustrate these embodiments.

Embodiment 1—Base Case

Figure 1A:
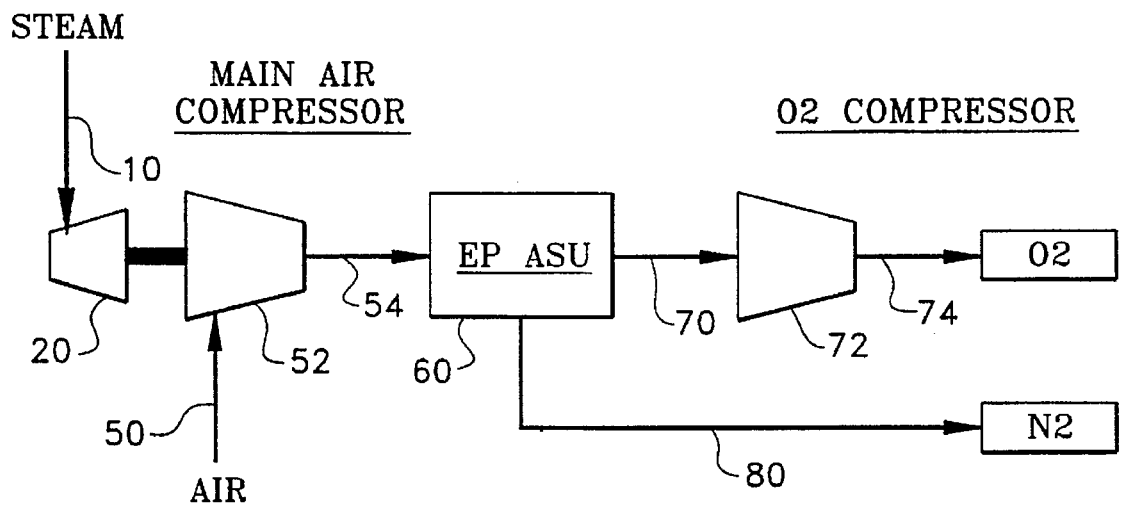
FIGS. 1A through 1D are schematic diagrams of several embodiments of the present invention.

In this embodiment, shown in FIG. 1A, excess steam from the remote gas process (line 10) is expanded in work expander 20 to generate work which is used in pad to drive main air compressor 52 of the elevated pressure air separation unit. In the air separation cycle, air (line 50) is compressed in main air compressor 52, cleaned to remove impurities which freeze at cryogenic temperatures and fed (line 54) to elevated pressure air separation cold box 60 which produces a high pressure nitrogen product (line 80) and a high pressure oxygen product (line 70). The oxygen product (line 70) is further compressed by compressor 72 and fed to the remote gas process (line 74). The high pressure nitrogen (line 80) may be reduced in pressure and vented to the atmosphere with no recovery of energy.

Equipment costs are lower because the feed and product pressures are higher and, therefore, the piping and exchangers are smaller. In addition, when the feed air is boosted to about 150 psia [1,030 kPa(absolute)] the oxygen compressor suction pressure is raised such that the oxygen machine can fit into one casing rather than two. The feed pressure would be optimized to allow for a single oxygen compressor casing as well as the best total fit of compression and steam driver equipment. For some remote gas processes, the air feed pressure may be selected to eliminate the need for an oxygen compressor, or the oxygen from the cold box may be pumped as a liquid to the required supply pressure.

Embodiment 2—Water Chilling

Figure 1B:
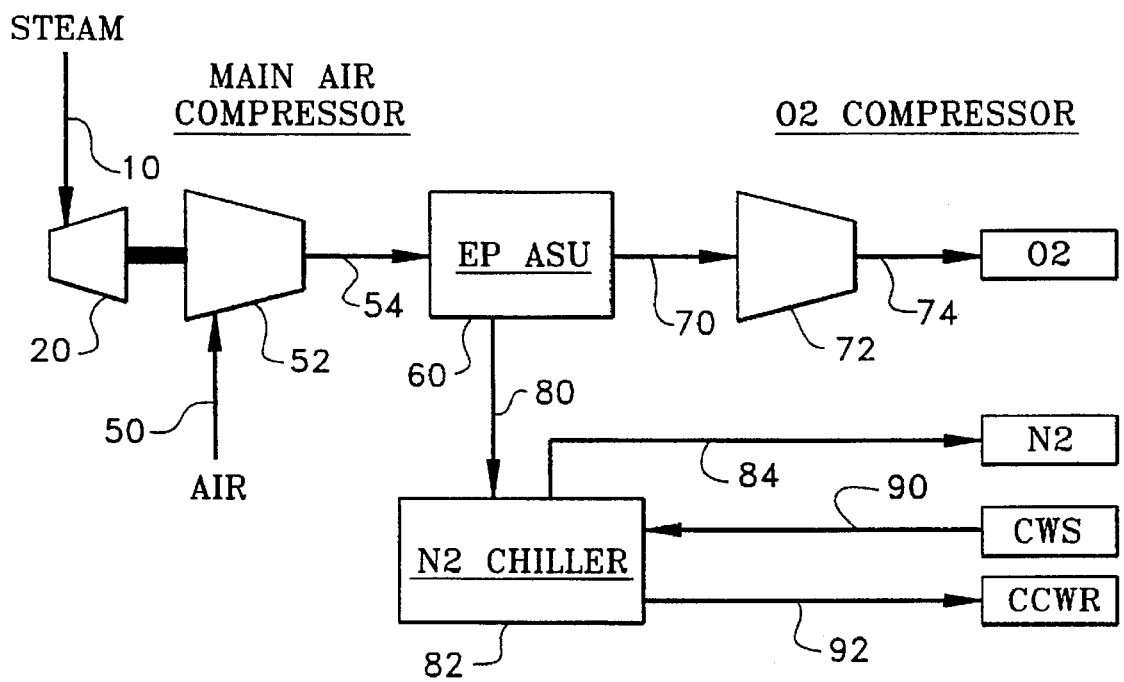

This embodiment, shown in FIG. 1B, is an extension of embodiment 1, but utilizes the high pressure nitrogen stream (line 80). The high pressure nitrogen stream (line 80) can be reduced in pressure or work expanded to slightly above atmospheric pressure and sent to waste nitrogen chilling tower 82 where the nitrogen rises countercurrent to the water being chilled (line 90). The bone dry nitrogen becomes water saturated at the top and the heat of vaporization of the water causes the water to be chilled. This chilled water (line 92) can be used in a variety of ways to reduce equipment costs such as direct or indirect compressor inter or after cooling. It can be used in a variety of services in remote gas process areas requiring chilling. Compressors for the remote gas and air separation processes can be gas turbine and/or steam turbine driven. The chilled water can be used for cooling the gas turbine suctions and/or cooling the steam turbine surface condensers. The system would be optimized such that chilled water usage produces the maximum savings in equipment costs.

Embodiment 3—Nitrogen Refrigeration

Figure 1C:
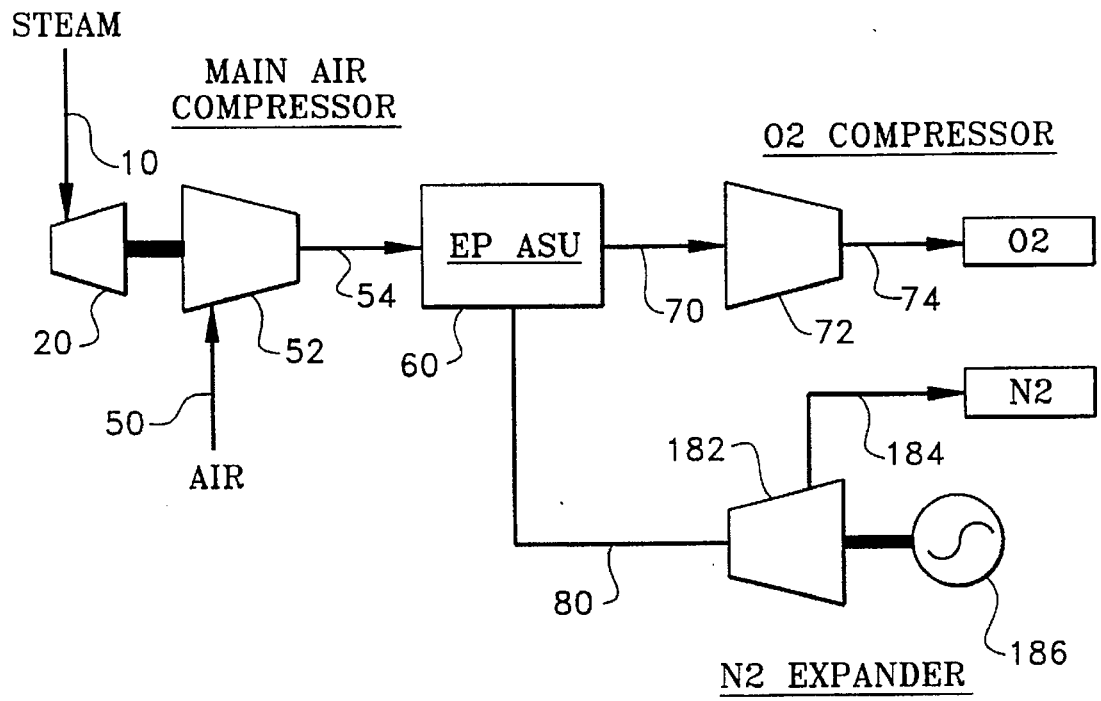

This embodiment, shown in FIG. 1C, is another extension of embodiment 1, except power producing expander 182 is used to recover energy from the high pressure nitrogen. The expander can be used to produce electrical power (186) which can be consumed by electric motors in the remote gas and air separation processes or can be coupled with air, oxygen, or other remote gas process compressors for energy recovery. The expanded nitrogen stream (line 184) is at cold temperatures and can be used as in embodiment 2. Optimization would reveal which of the many options for recovering energy from the air separation unit high pressure nitrogen would produce the biggest cost savings.

Embodiment 4—Heated Nitrogen Expansion

Figure 1D:
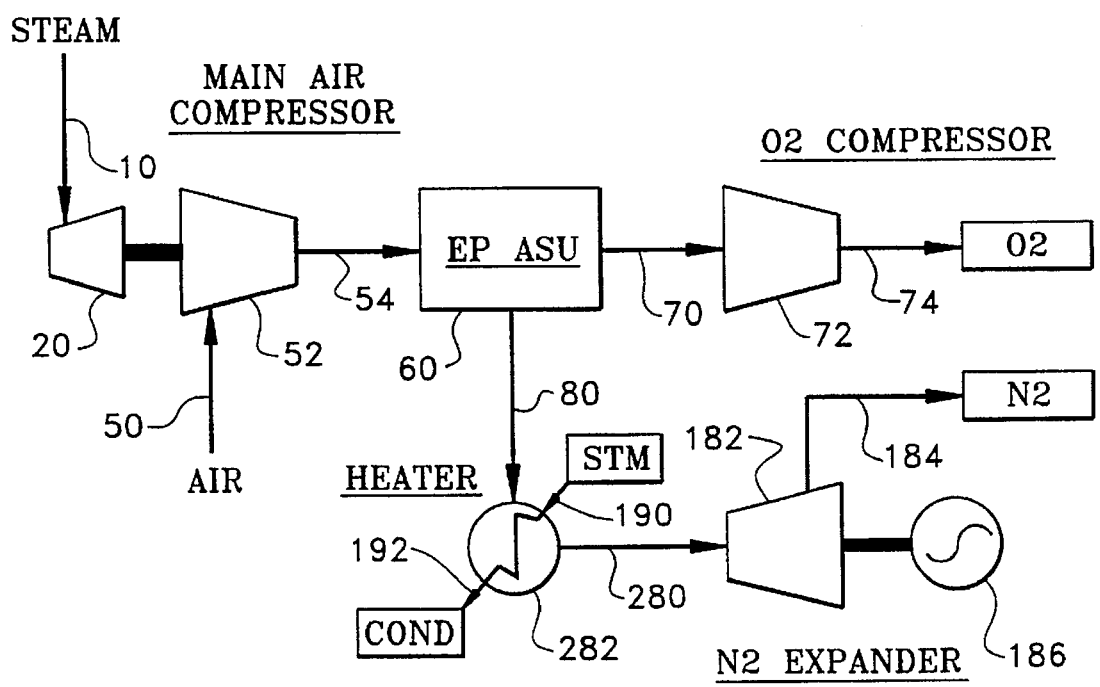

This option, shown in FIG. 1D, is still another extension of embodiment 1 except a portion of the excess steam (190) or other waste heat from the remote gas process is used to heat the high pressure nitrogen (80) in heat exchanger 282 prior to work expansion 182. The higher expander inlet temperature than in embodiment 3 produces more power, but a higher temperature from the expander may eliminate using the nitrogen for additional cooling. The amount of heating of the nitrogen can be adjusted to produce varying amounts of work in the expander and varying amounts of refrigeration in the expanded nitrogen. This option meets one of the objectives of the invention, to utilize excess energy (usually steam) from the remote gas process. The power can be utilized as in embodiment 3 to reduce capital costs.

In the above embodiments of the present inventions, the elevated pressure air separation unit has the advantage of lower capital cost. The power efficiency is lower with an elevated pressure air separation unit, but due to its low valuation for remote gas processes, it is not as important as reducing capital cost. Several corollaries of the basic invention further reduce equipment costs.

The present invention has been described with reference to several embodiments thereof. Such embodiments should not be viewed as a limitation on the present invention. The scope of which should be ascertained in the following claims.

We claim:

1. A process for the conversion of natural gas to produce higher molecular weight hydrocarbon products, wherein the natural gas is partially oxidized to produce a synthesis gas comprising carbon monoxide and hydrogen, wherein the synthesis gas is catalytically reacted to produce the higher molecular weight hydrocarbon products, wherein the conversion process generates excess steam and wherein oxygen used to partially oxidize the natural gas is produced by an air separation process, characterized by operating such air separation process at an elevated pressure so that the feed air to the air separation process is compressed to between 8 and 30 Bar(a) [800 and 3,000 kPa(absolute)]; expanding at least a portion of the excess steam generated by the conversion process to generate work and using at least a portion of the generated work to drive at least a portion of the compression requirements of the air separation process.

2. The process of claim 1 wherein the elevated pressure air separation process also produces high pressure nitrogen and wherein the high pressure nitrogen is reduced in pressure and fed to a water chilling tower.

3. The process of claim 2 wherein the high pressure nitrogen is reduced in pressure by expansion to generate work.

4. The process of claim 3 wherein said work is used to generate electricity.

5. The process of claim 3 wherein said work is used to drive compression requirements of the process.

6. The process of claim 1 wherein the elevated pressure air separation process also produces high pressure nitrogen and wherein the high pressure nitrogen is expanded to generate work.

7. The process of claim 6 wherein said work is used to generate electricity.

8. The process of claim 6 wherein said work is used to drive compression requirements of the process.

9. The process of claim 6 wherein the high pressure nitrogen is heated by another portion of the excess steam prior to work expansion.

10. The process of claim 9 wherein said work is used to generate electricity.

11. The process of claim 9 wherein said work is used to drive compression requirements of the process.

* * * * *